Feb. 19, 1974 W. H. JESSEL, JR., ET AL Plant Pat. 3,481
CHRYSANTHEMUM PLANT
Filed June 5, 1972
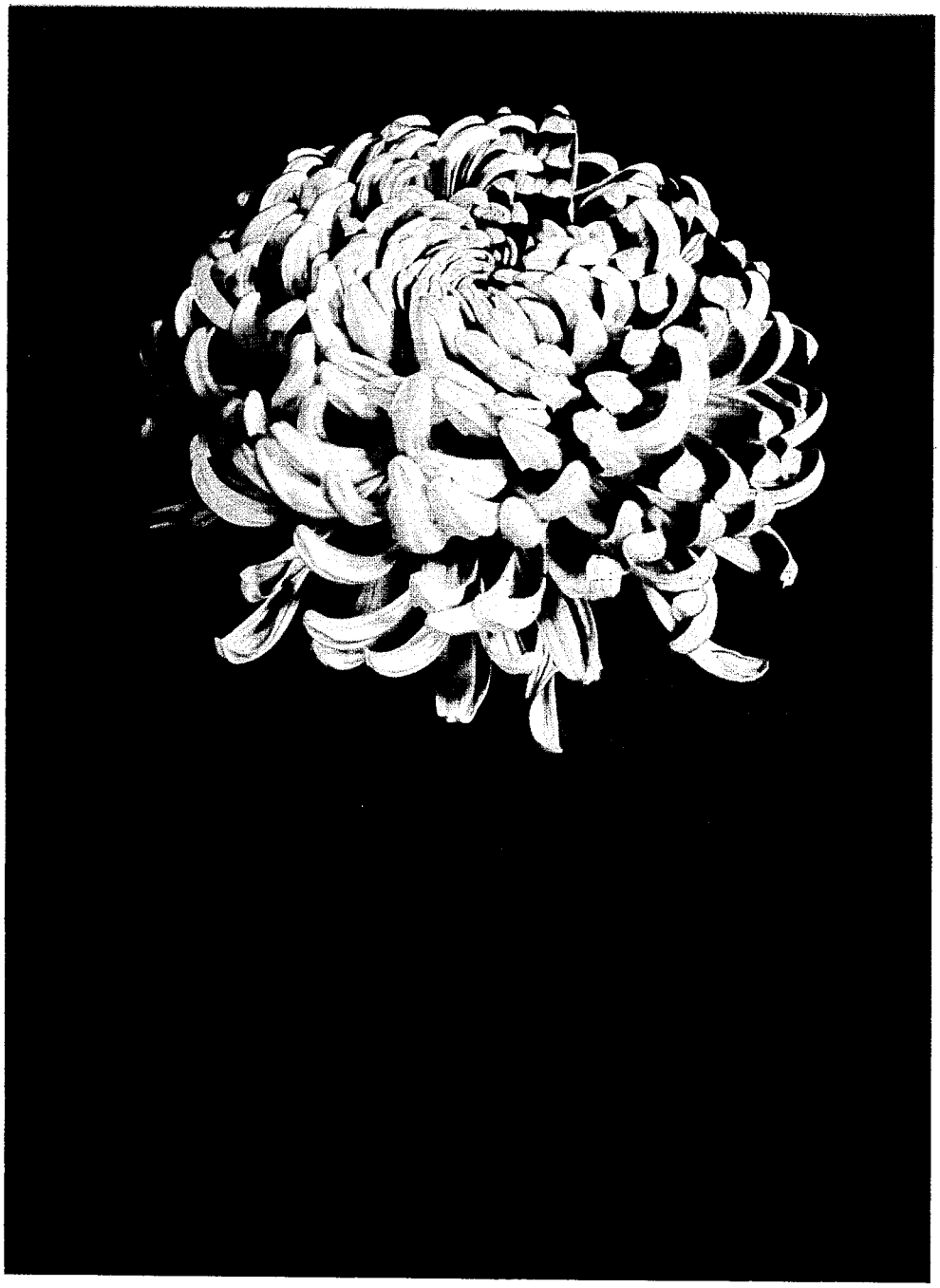

United States Patent Office

Plant Pat. 3,481
Patented Feb. 19, 1974

3,481
CHRYSANTHEMUM PLANT

Walter H. Jessel, Jr., Doylestown, and William E. Duffett, Akron, Ohio, assignors to Yoder Brothers, Inc., Barberton, Ohio Filed June 5, 1972, Ser. No. 259,997
Int. Cl. A01h 5/00
U.S. Cl. Plt.—79 1 Claim The present invention comprises a new and distinct cultivar of chrysanthemum plant known by the varietal name Gambit which is a seedling of #621003-1 × #3296. Both parents are unpatented and are identified for breeding purposes by the above breeding numbers.

This new cultivar offers the following characteristic features to standard chrysanthemum producers:

(1) It has good vigor and a strong stem.

(2) It has a medium large to large incurved flower.

(3) It has a bright bronze color. Many bronze standards presently available lack brightness and luster in their color.

(4) It is suitable for winter production in most areas of the United States. The list of suitable cultivars for this flowering period is limited at present.

(5) In California, besides its winter performance, it provides a bronze standard for spring. Detroit News, the most popular bronze standard in California, lacks vigor, uniform response, and good flower size during this period and does not begin to perform well until late spring and early summer.

(6) It ships well if harvested in the ⅓ to ½ open stage, and unlike many standards, it opens quite well in approximately three days with only clorox added to the water.

(7) It is very low temperature tolerant and will initiate and develop buds at 56°–58° F.

Other distinguishing features about this cultivar are:

(1) It will shatter (a) if allowed to open beyond the three-fourths stage before cutting, (b) if flowered in high temperature periods. Under high temperatures the petals develop a longitudinal petal roll and become tubular. In this form, shattering is most severe.

(2) It develops other flower form changes depending on environmental factors, primarily light and temperature. In Salinas, Calif., the flower develops a high crown because of the high light and cool temperature environment this area provides.

Under environmental conditions in Barberton, Ohio, it develops a high crown in late fall and early spring flowerings but if flowered under high temperatures, a flatter crown is developed. Also, under the low light conditions of December-January flowerings, the form of the flower is loose or more reflexed.

The new cultivar was selected from the progeny of the designated cross and when asexually reproduced by cuttings at Barberton, Ohio, has been found to retain its distinctive characteristics through successive propagations.

Our new cultivar when grown in the vicinity of Barberton, Ohio, responds as an early 9 week in late fall; a late 9 in midwinter, and a late 8 in early spring. In Salinas, Calif., it responds as a late 8 week cultivar from late fall through spring. The following detailed description is based on observations made of the new cultivar in a greenhouse in Barberton, Ohio. The response time, blooming period, color and total vigor may vary significantly with varying environmental conditions such as temperature, day length, and light intensity. Suggested flowering in the northern and western United States is from October through May; coastal California, October through May, in the southeastern and southwestern United States, December through March. The new cultivar is not recommended for outdoor culture in Florida.

The accompanying drawing shows the unique characteristics of our new cultivar, the color being as nearly true as possible with color illustrations of this type.

In the description which follows, color references are made to the Munsell Color Book, 1963 edition.

Botanical Classification: *Chrysanthemum morifolium*

Bloom:

*Size.*—5¾"

*Fully expanded.*—6¼"

*Borne.*—Singly on disbudded plants

*Stems.*—Strong

*Form.*—Incurve

*Permanence.*—10–12 days

*Color (Munsell)*—Center of flower: golden bronze, 2.5Y7/10 over yellow, 5Y8/10. Base of petals: yellow green, 2.5GY7/8. Inside of petals: bronze, 1.25YR4/12 over yellow, 5Y8/10. Reverse of petals: golden bronze, 2.5Y7/10 over yellow, 5Y8/10. Tonality from a distance: golden bronze. Discoloration: orange bronze, 5YR5/10 over yellow, 5Y8/10.

Petals:

*Texture.*— Smooth

*Appearance and form.*—Tubular at base, opening slowly to a deep ridged keel, tapering to a hooded tip

*Arrangement.*—Composite, whorled on a single receptacle

*Persistence.*—Resist shatter

*Fragrance.*—Typical chrysanthemum

Reproductive organs:

*Stamen, anthers.*—0–20

*Pollen.*—None to very scant

*Arrangement.*—Clustered in center of flower, if present

*Styles.*—Present both ray and disc florets

*Length.*—Short

*Ovaries.*—At the base of petal attached to receptacle

Plant:

*Form.*—Herbaceous

*Growth.*—Upright

*Height.*—Approximately 42" when given 5–6 long day weeks, and 14–15 weeks crop time as defined in the timetables of Yoder Brothers, Inc. for midwinter flowerings at Barberton, Ohio. Approximately 42" when given 3–4 long day weeks, and 12–13 week crop time as defined in the timetables of Yoder Brothers, Inc. for late fall and early spring flowerings at Barberton, Ohio.

*Spread.*—None when grown single stem to slight when grown pinched

Foliage:

*Top side.*—Very dark green, 7.5GY2/4

*Size.*—6¼" long, 3½" wide

*Quantity.*—Numerous
*Shape.*—Spatulate lobed
*Texture.*—Coarse
*Ribs and veins.*—Prominent
*Edge.*—Deeply indented
*Serration.*—Finely serrated
*Under side.*—Medium green, 7.5GY4/4
*Stipules.*—Moderately prominent.

We claim:

1. A new and distinct cultivar of chrysanthemum characterized particularly as to its uniqueness by its good vigor and strong stem; medium large to large incurved flower; its bright bronze, lustrous flower color; its suitability for winter production in most areas of the United States, and by its ability to be grown as a bronze standard for spring in California; by its excellent shipping qualities if harvested in the ⅓ to ½ open stage, opening quite well in approximately three days with only clorox added to the water, and by its very low temperature tolerance, with the new cultivar initiating and developing buds at 56°–58° F.

No references cited.

ROBERT E. BAGWILL, Primary Examiner